United States Patent
Donnay et al.

(10) Patent No.: US 10,463,303 B2
(45) Date of Patent: Nov. 5, 2019

(54) ADHESIVE PATCH FOR USE WITH REUSABLE MEDICAL DEVICES

(71) Applicant: St. Jude Medical, Cardiology Division, Inc., St. Paul, MN (US)

(72) Inventors: Nicholas M. Donnay, Maple Grove, MN (US); Lawrence D. Swanson, White Bear Lake, MN (US); Adam Fischbach, Inver Grove Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 206 days.

(21) Appl. No.: 15/404,445

(22) Filed: Jan. 12, 2017

(65) Prior Publication Data
US 2017/0238872 A1    Aug. 24, 2017

Related U.S. Application Data

(60) Provisional application No. 62/298,224, filed on Feb. 22, 2016.

(51) Int. Cl.
| | |
|---|---|
| *A61B 5/06* | (2006.01) |
| *A61M 25/02* | (2006.01) |
| *A61B 5/00* | (2006.01) |
| *A61B 34/20* | (2016.01) |
| *A61M 25/01* | (2006.01) |

(52) U.S. Cl.
CPC ............ *A61B 5/6833* (2013.01); *A61B 5/061* (2013.01); *A61B 5/062* (2013.01); *A61B 5/063* (2013.01); *A61M 25/02* (2013.01); *A61B 2034/2051* (2016.02); *A61B 2560/0412* (2013.01); *A61M 2025/0166* (2013.01); *A61M 2025/0266* (2013.01)

(58) Field of Classification Search
CPC .............. A61B 5/6833; A61B 5/68335; A61B 2560/0412
See application file for complete search history.

(56) References Cited

U.S. PATENT DOCUMENTS

| | | | | |
|---|---|---|---|---|
| 6,925,317 B1 * | 8/2005 | Samuels | ............ | A61B 5/14514 600/309 |
| 8,498,694 B2 * | 7/2013 | McGuire, Jr. | ........ | A61B 5/0086 600/344 |

(Continued)

FOREIGN PATENT DOCUMENTS

| | | |
|---|---|---|
| EP | 2520223 A1 | 11/2012 |
| WO | 0076575 A2 | 12/2000 |
| WO | 2013066854 A1 | 5/2013 |

*Primary Examiner* — Carrie R Dorna
(74) *Attorney, Agent, or Firm* — Armstrong Teasdale LLP

(57) ABSTRACT

An apparatus for use in securing a reusable medical device to an exterior surface of a patient's body includes a cushion, a first adhesive member, and a second adhesive member. The cushion includes a bottom side, a top side opposite the bottom side, and an opening adapted to receive at least a portion of the reusable medical device therein. The first adhesive member includes an upper adhesive surface and lower adhesive surface opposite the upper adhesive surface. The second adhesive member is interposed between the cushion and the first adhesive member, and includes a first adhesive surface and a second adhesive surface opposite the first adhesive surface.

18 Claims, 5 Drawing Sheets

(56) References Cited

U.S. PATENT DOCUMENTS

| | | | |
|---|---|---|---|
| 9,233,228 B1 | 1/2016 | Lelievre et al. | |
| 2009/0012473 A1* | 1/2009 | Stettler | A61B 5/14532 604/151 |
| 2009/0318793 A1 | 12/2009 | Datta et al. | |
| 2009/0318796 A1 | 12/2009 | Datta et al. | |
| 2014/0012102 A1* | 1/2014 | Das | A61B 5/08 600/309 |

* cited by examiner

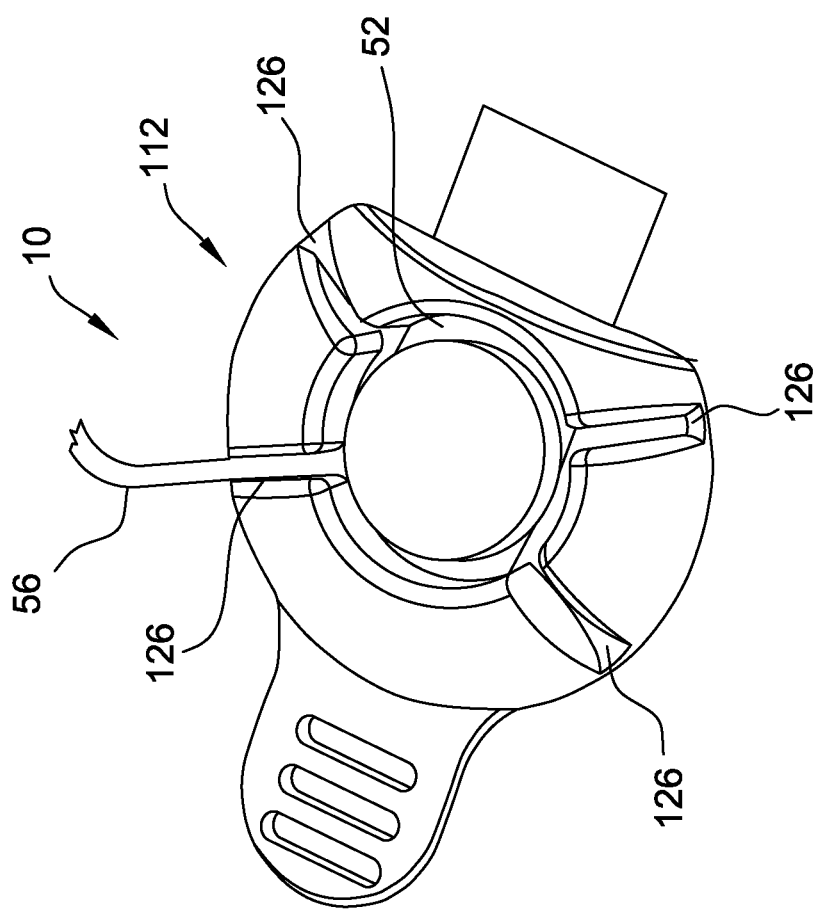

ADHESIVE PATCH FOR USE WITH REUSABLE MEDICAL DEVICES

CROSS-REFERENCE TO RELATED APPLICATIONS

This application claims the benefit of priority to U.S. Provisional Patent Application No. 62/298,224, filed Feb. 22, 2016, entitled "ADHESIVE PATCH FOR USE WITH REUSABLE MEDICAL DEVICES," the contents of which are hereby incorporated by reference in their entirety.

FIELD OF THE DISCLOSURE

The present disclosure relates to adhesive patches for use in securing reusable medical devices to a patient's body. More specifically, the present disclosure relates to apparatuses and methods for securing a reusable device such as a sensor to the exterior surface of a patient's body during a medical procedure.

BACKGROUND

Surface electrodes are employed in medical procedures for sensing electrical and/or magnetic fields used in tracking the location of medical devices within a patient's body. In cardiac mapping systems, such surface electrodes may be used for tracking the location of catheters, introducers, probes, and/or other medical devices inserted into the body. In the ENSITE PRECISION™ cardiac mapping system available from St. Jude Medical, Inc., for example, such surface electrodes may be used as part of a localization system that tracks the location of device(s) inserted into the body using electric and magnetic fields.

SUMMARY

In one aspect, an apparatus for use in securing a reusable medical device to an exterior surface of a patient's body is provided. The apparatus includes a cushion including a bottom side, a top side opposite the bottom side, and an opening adapted to receive at least a portion of the reusable medical device therein. The apparatus further includes a first adhesive member including an upper adhesive surface and lower adhesive surface opposite the upper adhesive surface, and a second adhesive member interposed between the cushion and the first adhesive member. The second adhesive member includes a first adhesive surface and a second adhesive surface opposite the first adhesive surface.

In another aspect, a method for securing a reusable medical device to an exterior surface of a patient's body is provided. The method includes providing a patch, the patch including a cushion including a bottom side, a top side opposite the bottom side, and an opening adapted to receive at least a portion of the reusable medical device therein, a first adhesive member including an upper adhesive surface and lower adhesive surface opposite the upper adhesive surface, and a second adhesive member interposed between the cushion and the first adhesive member, the second adhesive member including a first adhesive surface and a second adhesive surface opposite the first adhesive surface. The method also includes coupling the patch to the exterior surface of the patient's body via the lower adhesive surface of the first adhesive member, and coupling the reusable medical device to the patch via the first adhesive surface of the second adhesive member.

In a further aspect, an apparatus for use in securing a reusable medical device to an exterior surface of a patient's body is provided. The apparatus includes a cushion including a cushioning ridge at least partially surrounding an opening, the opening adapted to receive at least a portion of the reusable medical device therein, and at least one adhesive member configured to secure the reusable medical device within the opening of the cushion and secure the apparatus to the exterior surface of the patient's body.

BRIEF DESCRIPTION OF THE DRAWINGS

FIG. 5 is a perspective view of a patch with a cushion in accordance with another exemplary embodiment.

DETAILED DESCRIPTION

The present disclosure relates to apparatuses and methods for securing a reusable device such as a patient reference sensor (PRS) to an exterior surface of a patient's body during a medical procedure. For purposes of illustration, several exemplary embodiments will be described in detail in the context of a patch that supports a PRS for use in cardiac mapping procedures. It is contemplated, however, that the apparatuses and methods described herein can be utilized in other contexts.

Figure 1:
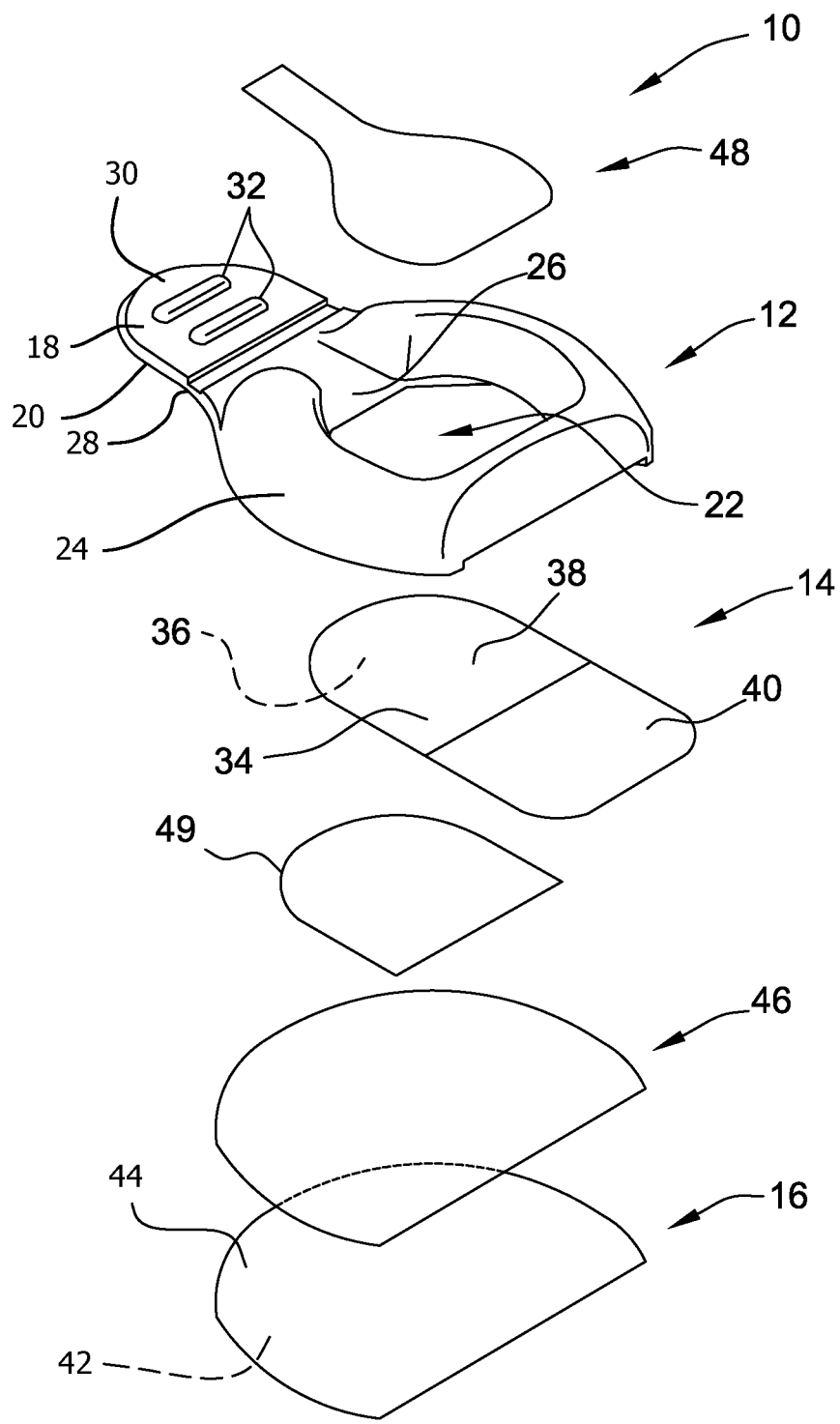
FIG. 1 is an assembly view showing a patch in accordance with an exemplary embodiment.

FIG. 1 is an assembly view showing a patch 10 in accordance with an exemplary embodiment. As shown in FIG. 1, patch 10 includes a cushion 12, a pull tab 14, and a patient-facing layer 16, which together can be used to releasably secure a sensor to a patient's body during a cardiac mapping procedure. In some procedures, for example, the patch 10 can be used to releasably secure a PRS (not shown in FIG. 1) to a patient's skin, and can be used in conjunction with a cardiac mapping system for locating medical devices within the body. Although only a single patch 10 is described and shown, it should be understood that multiple such patches 10 can be used. In some cardiac mapping procedures, for example, a first patch 10 can be used for securing a first PRS sensor to a patient at a location on the patient's back and a second patch 10 can be used for securing a second PRS sensor to the patient at a location on the patient's chest.

The cushion 12 includes a first or "top" side 18, a second or "bottom" side 20 opposite the top side 18, and an opening 22 that extends through the top and bottom sides 18, 20. A cushioning ridge 24 extends upwardly from the top side 18 of the cushion 12 and defines an internal space or valley that, as discussed in greater detail herein, is sized to match a profile of a PRS inserted therein from a location above the patch 10. The cushion 12 is made from a flexible material that serves to increase patient comfort when the patient is laying or resting against the rigid material of the PRS. In some embodiments, for example, the cushion 12 comprises a molded foam material that absorbs at least a portion of the patient's load when the patient is resting against the PRS during a procedure.

Figure 2:
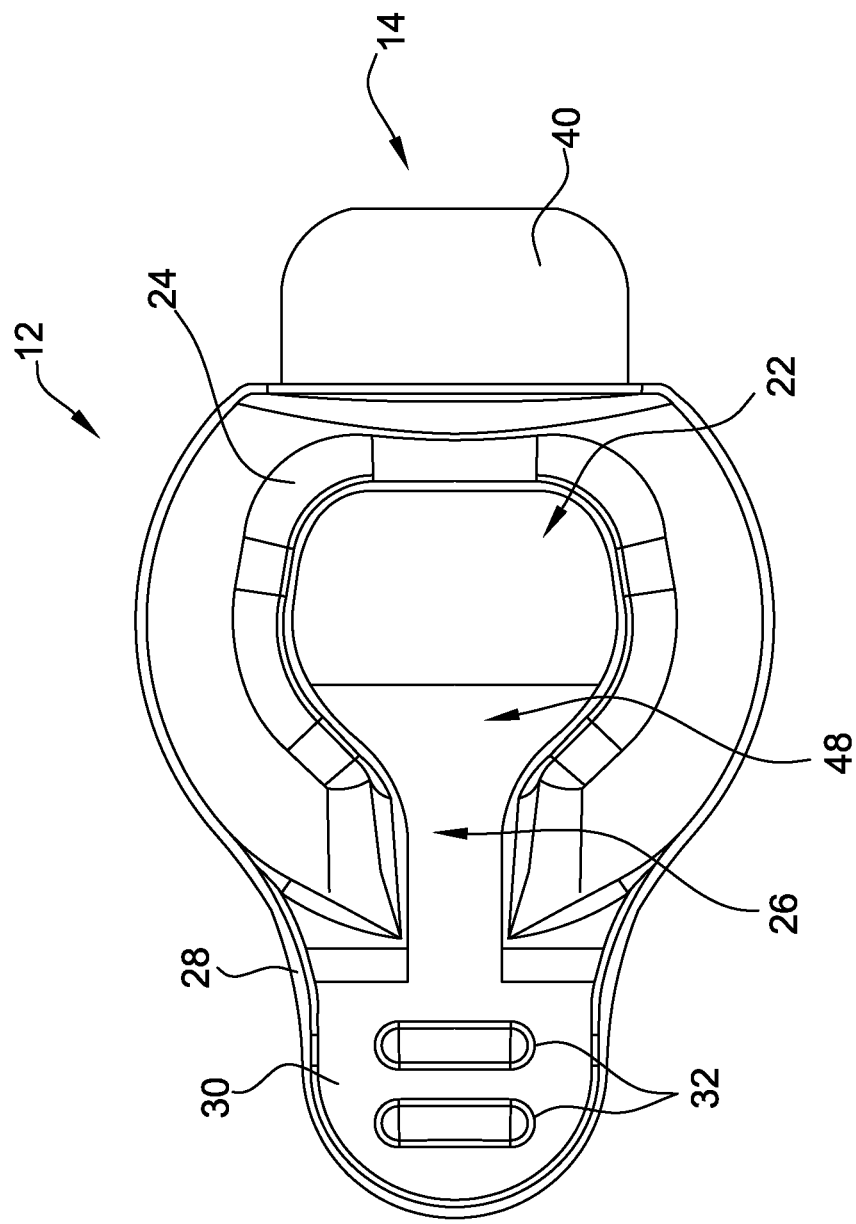
FIG. 2 is top schematic view of the patch shown in FIG. 1.

As can be further seen in conjunction with FIG. 2, the cushioning ridge 24 at least partially surrounds the opening 22. A channel 26 of the cushion 12 is configured to permit a wire or cable (not shown) to exit from the cushion 12 (e.g., towards the patient's shoulder for a chest patch) and out of the way to prevent interference with a fluoroscopic imaging system. The channel 26 is shown defined in the upper side 18 of the cushion 12. In an alternative embodiment, the channel is defined in the bottom side 20 of the cushion 12. A tab 30 extends laterally from the cushion 12 along an edge 28 thereof. The tab 30 is provided to permit the later removal of the cushion 12 from the patient-facing layer 16 at the conclusion of a mapping procedure, allowing the sensor to be decoupled from the patient's skin for later reuse. A number of bumps or ridges 32 located on the tab 30 are provided to permit the user to easily grip the tab 30 during removal.

The pull tab 14 can comprise a double-sided adhesive structure having a first surface 34 and a second surface 36. The first surface 34 of the pull tab 14 includes a first region 38 including an adhesive material that is used to secure the pull tab 14 to the bottom side 20 of the cushion 12. The first region 38 is further configured to enable adhesive attachment of a sensor to the patch 10. At least a portion of the first region 38 aligns with the opening 22 of the cushion 12 when the patch 10 is constructed, such that the adhesive of the first region 38 is exposed through the opening 22. A second (i.e., non-sticky) region 40 of the first surface 34 is generally devoid of adhesive, and as discussed further herein, can be later used along with tab 30 to facilitate removal of a sensor from the patch 10. In some embodiments, the pull tab 14 comprises a double-sided adhesive mounting tape such as the TESA™ bond and detach tape 70410 available from the company of TESA SE, which allows the pull tab 14 to be easily removed after bonding by stretching the adhesive in a direction along its bonding plane. In one embodiment, the second surface 36 of the pull tab 14 is fully adhesive. In another embodiment, the second surface 36 also includes the first region 38 and the second region 40, such that a portion of the second surface 36 (i.e., the first region 38) is adhesive and a portion of the second surface 36 (i.e., the second region 40) is non-adhesive.

The patient-facing layer 16 comprises a double-adhesive structure including a first, patient-facing side 42 and a second, upward-facing side 44 opposite the patient-facing side 42. In use, the patient-facing layer 16 is configured to provide sufficient strength to support the patch 10 against the patient's skin. A transfer layer 46 containing a hypoallergenic, pressure-sensitive acrylate adhesive can be used to adhere the upper-facing side 44 of the patient-facing layer 16 to the pull tab 14. In some embodiments, a double-sided, nonwoven tape including a woven backing material, such as acrylic, and a suitable biocompatible adhesive material, such as acrylate, may be used. An example of such material is the 3M™ 9917 medical tape available from 3M, Inc.

When assembled together, the pull tab 14 is situated between the bottom side 20 of the cushion 12 and the upward-facing side 44 of the patient-facing layer 16. The pull tab 14 is secured to the patient-facing layer 16 via adhesion of the transfer layer 46 to the second (adhesive) surface 36, and to the cushion member 12 via adhesion of the first region 38 to the bottom side 20 of the cushion 12. A liner 48 adapted to fit within the opening 22 of the cushion member 12 is used to cover the first adhesive surface 34 prior to its use.

In some embodiments, a non-adhesive member 49, also referred to as a releasing member, is positioned between the pull tab 14 and the patient-facing layer 16 (e.g., between the upward-facing side 44 of the patient-facing layer and the second surface 36 of the pull tab 14). The releasing member 49 is configured to reduce an amount of force F (described further herein) required to release a medical device (e.g., a PRS) from the patch 10 (e.g., from the first region 38 of the pull tab 14). The releasing member 49 may be constructed from a polyester material.

Figure 3:
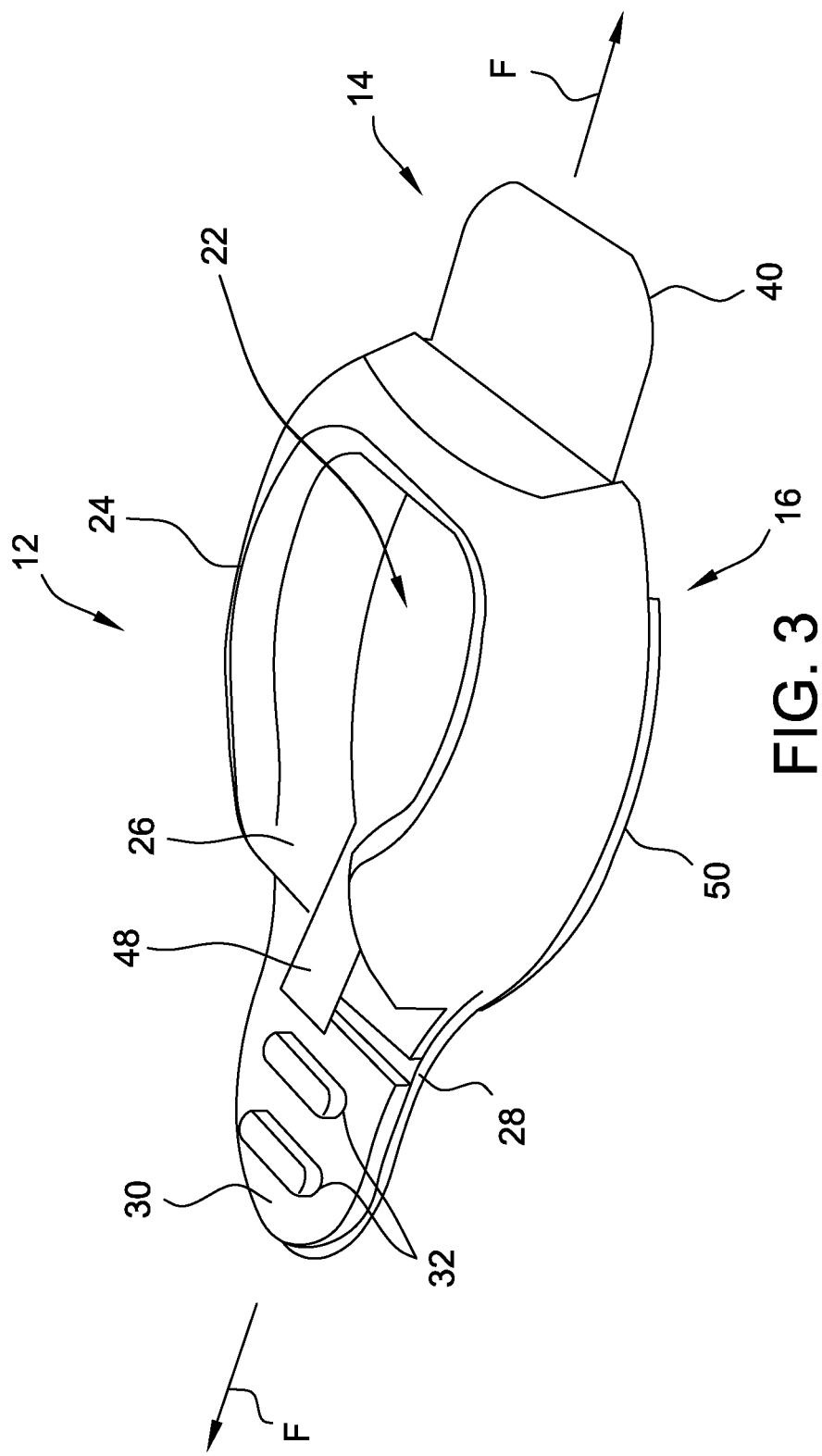
FIG. 3 is a perspective view of the patch shown in FIGS. 1 and 2 with an adhesive pull tab and a patient-facing layer coupled to a cushion prior to use of the patch.

FIG. 3 is a perspective view showing the adhesive pull tab 14 and patient-facing layer 16 coupled to the cushion 12. FIG. 3 may represent, for example, a fully-assembled patch 10 prior to attachment to the patient's skin. In preparation for use, the patient's skin is cleaned and a liner 50 located adjacent to the patient-facing surface 44 of layer 16 is removed to expose the adhesive. The patch 10 is oriented appropriately (e.g., with the pull tab 30 facing towards the patient's head) and is then adhesively secured in place via layer 16. Once in position on the patient, the pull tab liner 48 is removed to expose the adhesive located on the first region 38. The first (adhesive) region 38 is exposed through the opening 22 of the cushion 12. Once removed, a sensor (e.g., a PRS 52 as shown, for example, in FIGS. 4 and 5) is then inserted into the internal space or valley formed by the cushioning ridge 24.

Figure 4:
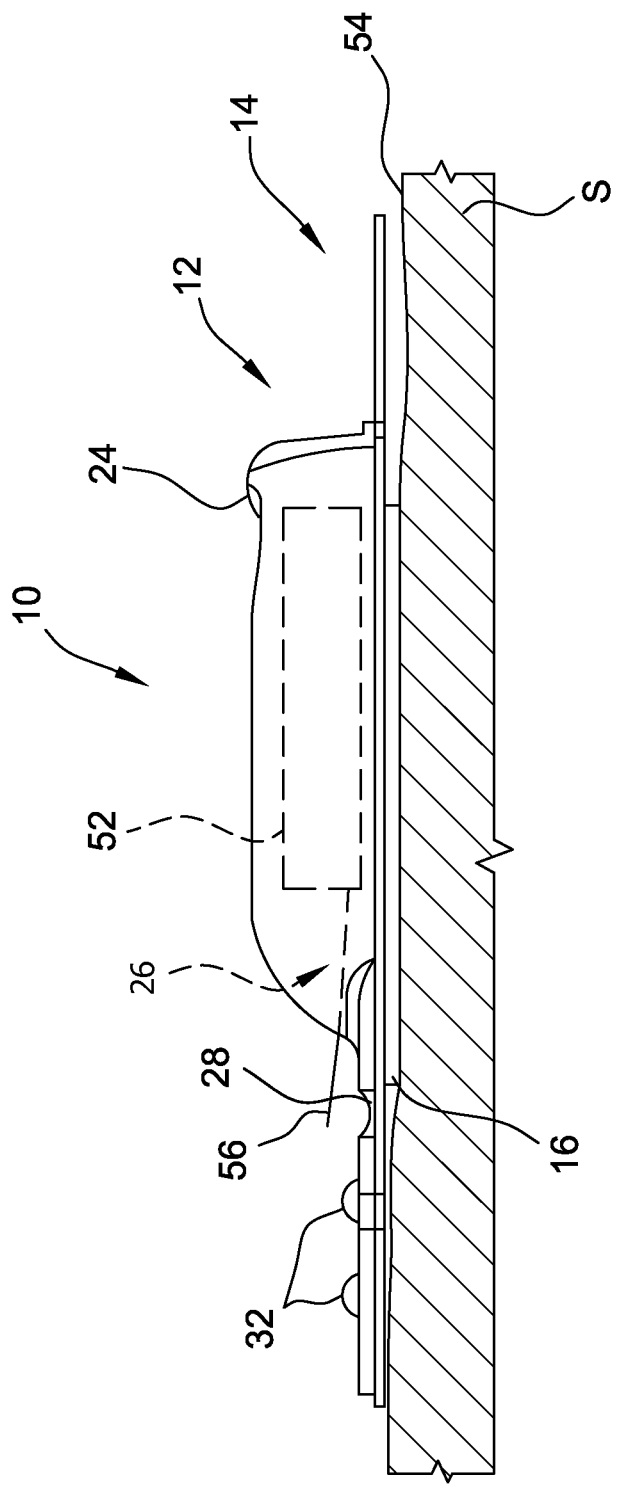
FIG. 4 is a side schematic view of the patch shown in FIGS. 1-3 adhesively coupled to a sensor and to an exterior surface of a patient's body.

FIG. 4 is a side schematic view showing the patch 10 adhesively coupled to a sensor 52 and to an exterior surface 54 of a patient's skin S. As can be seen in FIG. 4, the channel 26 in the cushion 12 provides a means for a sensor cable 56 to route away from the patch 10 in a particular direction (e.g., towards the patient's head). Although the cushion 12 depicted includes a single channel for routing the sensor cable 56 away from the patch 12, in other embodiments multiple such channels may be used. In one alternative embodiment, as shown in FIG. 5, for example, a cushion 112 may be provided with multiple channels 126, allowing one or multiple sensor cable(s) 56 to be routed away from the patch 10 at different locations.

To remove the sensor 52 from the patch 10, the user may grip the two tabs 14, 30 and apply an upwardly directed force (i.e., a force directed away from the patient's skin S), causing the cushion 12, the pull tab 14, and the sensor 52 to detach from the patient-facing layer 16. In a further step, the user may grip tab 30 and the second (non-adhesive) portion 40 of the pulltab 14 with their fingers and then pry the two tabs 14, 30 apart from each other in opposite directions, as indicated generally by force F in FIG. 3. When a sufficient force F is applied to the two tabs 14, 30, the stretching of the pull tab 14 along the plane of the bond causes the bond to break, allowing the user to easily remove the sensor 52 from within the cushion 12. The cushion 12 and pull tab 14, along with the patient-facing layer 16, can then be discarded.

Although several embodiments of this disclosure have been described above with a certain degree of particularity, those skilled in the art could make numerous alterations to the disclosed embodiments without departing from the spirit or scope of this disclosure.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present disclosure, and do not create limitations, particularly as to the position, orientation, or use of the embodiments of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the disclosure as defined in the appended claims.

What is claimed is:

1. An apparatus for use in securing a medical device to an exterior surface of a patient's body, the apparatus comprising:
a cushion including a bottom side, a top side opposite the bottom side, and an opening adapted to receive at least a portion of the medical device therein;
a first adhesive layer including an upper adhesive surface and a lower adhesive surface opposite the upper adhesive surface; and
a second adhesive layer interposed between the cushion and the first adhesive layer, the second adhesive layer including a first adhesive surface and a second adhesive surface opposite the first adhesive surface, the second adhesive layer including i) a first region defined at least in part on the first adhesive surface and ii) a second, non-adhesive region adjacent the first region and facing the same direction as the first region, wherein at least a portion of the first region is aligned with the opening of the cushion, and wherein at least a portion of the second, non-adhesive region extends outwards beyond the cushion.

2. The apparatus of claim 1, wherein at least a portion of the first region aligns with the opening of the cushion to expose the first adhesive surface through the opening.

3. The apparatus of claim 2, further comprising a liner coupled to the top side of the cushion and to the portion of the first region aligned with the opening of the cushion.

4. The apparatus of claim 1, further comprising a third adhesive layer interposed between the first adhesive layer and the second adhesive layer, the third adhesive layer comprising a pressure-sensitive adhesive material.

5. The apparatus of claim 1, further comprising a non-adhesive layer interposed between the first adhesive layer and the second adhesive layer, the non-adhesive layer comprising a non-adhesive material configured to reduce a force required to separate the first adhesive layer from the cushion upon removal of the apparatus from the patient's body.

6. The apparatus of claim 1, wherein the cushion further comprises a ridge at least partially surrounding the opening.

7. The apparatus of claim 6, wherein the ridge defines a channel configured to receive a portion of the medical device therein.

8. The apparatus of claim 1, wherein the cushion further comprises a tab extending from an edge thereof.

9. The apparatus of claim 1,
wherein the cushion is configured to be separated from the second adhesive layer by applying a lateral force to the second region of the second adhesive layer and an opposite lateral force to a tab of the cushion.

10. A method for securing a medical device to an exterior surface of a patient's body, the method comprising:
providing a patch, the patch including a cushion including a bottom side, a top side opposite the bottom side, and an opening adapted to receive at least a portion of the medical device therein, a first adhesive layer including an upper adhesive surface and lower adhesive surface opposite the upper adhesive surface, and a second adhesive layer interposed between the cushion and the first adhesive layer, the second adhesive layer including a first adhesive surface and a second adhesive surface opposite the first adhesive surface, wherein the second adhesive layer of the patch further includes a first region defined at least in part on the first adhesive surface, and wherein at least a portion of the first region aligns with the opening of the cushion to expose the first adhesive surface through the opening;
coupling the patch to the exterior surface of the patient's body via the lower adhesive surface of the first adhesive layer;
removing a liner coupled to the top side of the cushion and to the portion of the first region aligned with the opening of the cushion to expose the first region; and
coupling the medical device to the patch via the first adhesive surface of the second adhesive layer by coupling the medical device to the portion of the first region exposed through the opening of the cushion.

11. The method of claim 10, further comprising de-coupling the medical device from the patch after use.

12. The method of claim 11, wherein de-coupling the medical device from the patch after use comprises applying a lateral force to the cushion and applying an opposing lateral force to the second adhesive layer.

13. The method of claim 12, wherein de-coupling the medical device from the patch after use further comprises separating the cushion from the second adhesive layer upon application of the lateral force and the opposing lateral force.

14. An apparatus for use in securing a medical device to an exterior surface of a patient's body, the apparatus comprising:
a cushion including a cushioning ridge at least partially surrounding an opening, the opening adapted to receive at least a portion of the medical device therein; and
at least one adhesive layer comprising a first region and a second region, the first region being adhesive, the second region being non-adhesive, the first region and the second region facing the same direction and positioned on opposite sides of the cushioning ridge, at least a portion of the first region aligned with the opening of the cushion, at least a portion of the second region extending outwards beyond the cushion, the at least one adhesive layer configured to secure the medical device within the opening of the cushion at the first region of the at least one adhesive layer and secure the apparatus to the exterior surface of the patient's body.

15. The apparatus of claim 14, wherein the at least one adhesive layer comprises a first adhesive surface, wherein the cushion is coupled to the first adhesive surface and a portion of the first adhesive surface is exposed through the opening of the cushion.

16. The apparatus of claim 15 further comprising a liner coupled to the cushion and to the portion of the first adhesive surface exposed through the opening of the cushion.

17. The apparatus of claim 14, wherein the ridge defines a channel configured to receive a portion of the medical device therein.

18. The apparatus of claim 14, wherein the cushion is configured to be separated from the at least one adhesive layer by applying a lateral force to the at least one adhesive layer at the second region and an opposite lateral force to the cushion.

* * * * *